(12) United States Patent
Li et al.

(10) Patent No.: US 10,562,005 B2
(45) Date of Patent: Feb. 18, 2020

(54) METHOD FOR GAS SEPARATION (71) Applicants: THE UNIVERSITY OF WESTERN AUSTRALIA, Crawley (AU); CHEVRON U.S.A. INC., San Ramon, CA (US)

(72) Inventors: Gang Li, Crawley (AU); Eric Freemantle May, Crawley (AU); Paul Anthony Webley, Carlton (AU); Stanley Hsing-Wei Huang, San Ramon, CA (US); Kaman Ida Chan, San Ramon, CA (US)

(73) Assignees: Gas Capture Technologies, Cockburn Central, Western Australia (AU); University of Western Australia, Crawley, Western Australia (AU)

( * ) Notice: Subject to any disclaimer, the term of this patent is extended or adjusted under 35 U.S.C. 154(b) by 0 days.

(21) Appl. No.: 15/535,692

(22) PCT Filed: Sep. 24, 2015

(86) PCT No.: PCT/AU2015/000588
§ 371 (c)(1),
(2) Date: Jun. 13, 2017

(87) PCT Pub. No.: WO2016/094929
PCT Pub. Date: Jun. 23, 2016

(65) Prior Publication Data
US 2017/0348670 A1 Dec. 7, 2017

(30) Foreign Application Priority Data
Dec. 17, 2014 (AU) ................. 2014905107

(51) Int. Cl.
| | | |
|---|---|---|
| *B01D 53/047* | (2006.01) | |
| *C07C 7/12* | (2006.01) | |
| *B01J 20/18* | (2006.01) | |
| *B01J 20/04* | (2006.01) | |
| *B01J 20/06* | (2006.01) | |
| *B01J 20/22* | (2006.01) | |
| *B01J 20/16* | (2006.01) | |
| *C07C 7/13* | (2006.01) | |
| *B01D 53/04* | (2006.01) | |

(52) U.S. Cl.
CPC .......... *B01J 20/186* (2013.01); *B01D 53/047* (2013.01); *B01J 20/041* (2013.01); *B01J 20/06* (2013.01); *B01J 20/165* (2013.01); *B01J 20/226* (2013.01); *C07C 7/12* (2013.01); *C07C 7/13* (2013.01); *B01D 53/0462* (2013.01); *B01D 53/0476* (2013.01); *B01D 2253/106* (2013.01); *B01D 2253/1085* (2013.01); *B01D 2253/116* (2013.01); *B01D 2253/204* (2013.01); *B01D 2253/306* (2013.01); *B01D 2253/308* (2013.01); *B01D 2253/31* (2013.01); *B01D 2253/311* (2013.01); *B01D 2256/245* (2013.01); *B01D 2257/102* (2013.01); *B01D 2259/40013* (2013.01); *B01D 2259/40043* (2013.01)

(58) Field of Classification Search
None
See application file for complete search history.

(56) References Cited

U.S. PATENT DOCUMENTS

| | | | | |
|---|---|---|---|---|
| 4,554,398 A | * | 11/1985 | Barthomeuf | C07C 7/13 208/310 Z |
| 5,616,170 A | * | 4/1997 | Ojo | B01D 53/02 95/101 |
| 5,669,958 A | | 9/1997 | Baker et al. | |
| 6,531,103 B1 | * | 3/2003 | Hakka | C10G 21/27 208/208 R |
| 8,540,800 B2 | | 9/2013 | Liu et al. | |
| 2005/0045030 A1 | | 3/2005 | Tonkovich et al. | |
| 2009/0263621 A1 | * | 10/2009 | Chang | B01D 53/28 428/116 |
| 2011/0315012 A1 | | 12/2011 | Kuznicki et al. | |
| 2012/0222552 A1 | | 9/2012 | Ravikovitch et al. | |
| 2015/0367321 A1 | * | 12/2015 | Wang | B01J 20/16 95/139 |

FOREIGN PATENT DOCUMENTS

EP 1216959 A2 6/2002

OTHER PUBLICATIONS

International Search Report and Written Opinion dated Nov. 9, 2015, or PCT Application No. PCT/AU2015/000588.
European Search Report (EP 3233246), dated Nov. 15, 2018.

* cited by examiner

*Primary Examiner* — Tam M Nguyen
(74) *Attorney, Agent, or Firm* — Gregory L. Porter; Hunton Andrews Kurth LLP (57) ABSTRACT

A method for separating at least one hydrocarbon from a feed containing a mixture of at least one hydrocarbon and nitrogen, comprising contacting the feed with an adsorbent comprising a porous support wherein the porous support comprises exchangeable cations and at least a portion of the exchangeable cations are organic cations.

8 Claims, 8 Drawing Sheets

METHOD FOR GAS SEPARATION

TECHNICAL FIELD

A method for separating at least one hydrocarbon from a feed containing a mixture of at least one hydrocarbon and nitrogen.

BACKGROUND ART

The following discussion of the background art is intended to facilitate an understanding of the present invention only. The discussion is not an acknowledgement or admission that any of the material referred to is or was part of the common general knowledge as at the priority date of the application.

Methane, $CH_4$ is the primary component of natural gas. It is both a valuable source of energy and potent greenhouse gas, with 21 times the global warming potential of carbon dioxide, $CO_2$. Nitrogen, $N_2$, is a common impurity in natural gas, varying from 0.5% to 25% by volume, depending on the source. This impurity has no energy content, no global warming potential, and needs to be removed from the natural gas to varying degrees to meet product sales specifications. Its removal is particularly important in the production of liquefied natural gas (LNG).

The separation of $N_2$ and $CH_4$ is challenging because they are molecules with very similar physical properties such as molecular size (0.364 and 0.380 nm respectively) and normal boiling point (−196 and −161° C., respectively). Conventionally, the removal of $N_2$ during LNG production is performed through cryogenic distillation, which is an expensive and energy intensive process. The removed $N_2$ must be disposed of and generally this is done by venting the $N_2$ to atmosphere. However, the purity of this vent is limited by the similarity of the physical properties of $N_2$ and $CH_4$. A $N_2$ vent stream containing about 2% $CH_4$ can be achieved with a single stage of cryogenic distillation. However, the magnitude of the vent stream (~50 tonnes/hour per 5 million tonne per annum LNG train) means that such a $CH_4$ concentration corresponds to a significant amount of wasted energy and source of greenhouse gas emissions.

Adsorption technologies based on molecular diameter differences have been attempted for $CH_4$ capture. However, separation of $CH_4$ and $N_2$ is very challenging because of their very close molecular diameters (3.80 Å vs 3.64 Å).

SUMMARY OF INVENTION

In accordance with the present invention, there is provided a method for separating at least one hydrocarbon from a feed containing a mixture of at least one hydrocarbon and nitrogen, comprising contacting the feed with an adsorbent comprising a porous support wherein the porous support comprises exchangeable cations and at least a portion of the exchangeable cations are organic cations.

It will be appreciated that the method of the present invention may not remove all of the at least one hydrocarbon from the mixture.

It will be appreciated that the mixture containing at least one hydrocarbon and nitrogen may contain other gases.

Preferably, the at least one hydrocarbon is selected from C1-C4 saturated or unsaturated hydrocarbons. More preferably, the at least one hydrocarbon is selected from a group containing methane, ethane, propane, butane, iso-butane, methylene, ethylene and propylene. Still preferably, the at least one hydrocarbon is selected from methane and ethane. In a preferred form of the present invention, the at least one hydrocarbon is methane.

In accordance with the present invention, there is provided a method for separating methane from a feed containing a mixture of methane and nitrogen, comprising contacting the feed with an adsorbent comprising a porous support, wherein the porous support comprises exchangeable cations, wherein at least a portion of the exchangeable cations are organic cations.

It will be appreciated that the method of the present invention may not remove all of the methane from the mixture.

It will be appreciated that the mixture containing methane and nitrogen may contain other gases.

The porous support may be selected from the group comprising silicates such as aluminosilicates, zeolites, zeolite-like metal-organic frameworks, molecular sieves, titanosilicates, layered hydroxides or hydrotalcites.

Alternatively, the porous support may be selected from the group comprising coordinated polymeric materials, including metal organic frameworks or carbonaceous materials.

It will be appreciated that there may be overlap between the types of porous supports described. For example, some molecular sieves are also aluminosilicates and some aluminosilicates are also molecular sieves.

Preferably, the porous support is a zeolite. Zeolites are crystalline aluminosilicates with open three dimensional framework structures built of, for example, $SiO_4$ and $AlO_4$ tetrahedra linked to each other by sharing all the oxygen atoms to form regular intra-crystalline cavities and channels of molecular dimensions. The electrovalence of the aluminium-containing tetrahedra is balanced by the inclusion of a cation, usually an alkaline metal or alkaline earth metal. It will be appreciated that zeolites may also comprise building blocks of $TiO_4$, $GaO_4$ and $FeO_4$.

The International Zeolite Association has recognized 229 families of zeolites. It is believed that about 67 naturally occurring zeolite frameworks are known. The number of synthetic zeolites grows regularly and many naturally occurring zeolites can now be synthesized.

The zeolite may be a natural zeolite or a synthetic zeolite. Zeolites that may be used in the present invention include ferrierite, brewsterite, stilbite, dachiardite, epistilbite, heulandite, chabazite and clinoptilolite.

In one form of the invention, the zeolite has faujasite topology. In an alternate form of the invention, the zeolite has Linde type A topology. In an alternate form of the invention, the zeolite has chabazite topology. Other suitable topologies include GME, LTL, MEI, MOZ and DFO as listed by the Structure Commission of the International Zeolite Association (http://izasc.ethz.ch/fmi/xsl/IZA-SC/ft.xsl).

Zeolites are distinguished by their Si:Al ratios. Zeolites with low ratios (~1:1) are termed X zeolites and those with high ratios (>1.5:1), Y zeolites. Commercially available Y zeolites include: CBV 100 (2.5:1); CBV 712 (6:1) and CBV720 (15:1).

An X zeolite with sodium cations is commonly designated NaX and a Y zeolite with sodium cations is commonly designated NaY.

It will be appreciated that the Si:Al ratio will have an effect on the number of cations per unit cell of the zeolite. The substitution of trivalent aluminum ions for a fraction of the tetravalent silicon ions at lattice positions results in a network that bears a net negative charge that is compensated by positively charged counter-ions. Thus, a lower ratio means a higher cation density. If the Si/Al ratio is too high, the low cation density may not be sufficient to accommodate enough organic cations.

It will be appreciated that the pore aperture size of the zeolite should be larger than the dimension of the organic cation to allow for the transfer of the organic cation into the cavity. As an example, tetramethylammonium (TMA) cations have a diameter of approximately 6 Å. Consequently, it is possible to exchange sodium ions with TMA ions in large pore zeolites for example, FAU types. It will be appreciated that if the dimensions of the organic cation and the pore aperture are close, such an ion exchange may not be experimentally viable due to limitation of mass transfer kinetics.

It will be appreciated that porous supports suitable for use in the practice of the invention are those with pore diameters large enough to adsorb a hydrocarbon of interest. Diameters of exemplary hydrocarbons include:

monomethylammonium—3.9 Å (estimated);
trimethylammonium—5.4 Å (estimated); and
tetramethylammonium—6 Å.

The zeolite is preferred to have a large accessible pore volume. As the dimensions of organic cations are much bigger than the metal cations, e.g. $Na^+$, $K^+$, $Ca^{2+}$ found in normal zeolites, a sufficiently large pore volume is required to accommodate multiple organic cations per unit cell; otherwise, there will not be enough room for a higher cation exchange rate.

The Si/Al ratio will have an effect on the percentage of metal cations that can be exchanged by organic cations (ion exchange capacity). It would therefore be understood by a person skilled in the art that the ion exchange capacity of the zeolite would be increased by reducing the Si/Al ratio, thus providing an increased number of exchange sites. The applicant has discovered however, that if the Si/Al ratio is too low, the cation density may be too high to allow for higher degree of cation exchange due to space hindrance and diffusion limitation. This would result in excess metal cations sitting unexchanged in the cavity of the zeolites, leading to reduced $CH_4$-over-$N_2$ adsorption performance. It is therefore preferable to balance the number of exchange sites with the cation density.

Preferably, the zeolite is a Y zeolite. More preferably, the zeolite has a Si/Al ratio of 2-20. More preferably, the zeolite has a Si/Al ratio of 2.5-15. More preferably, the zeolite has a Si/Al ratio of 2.5-6.

It will be appreciated that it is desirable that the organic cations have the physical properties that are specified for the adsorption of target molecules. Where $CH_4$-over-$N_2$ selectivity is desired, the organic cations preferably have low charge density and low polarity for the purpose of substantially reducing the adsorption energy of $N_2$. For example, $TMA^+$ has the same charge as $Na^+$ but a much larger size and thus the density of the charge is much smaller than that of the sodium cation, leading to increased selectivity.

Preferably, the organic cation is an ionic liquid.

Preferably, the organic cation is selected from the following; substituted ammonium cations, substituted phosphonium cations and organic nitrogen-containing cations.

Preferably, the substituted ammonium cation is an alkylammonium cation.

Preferably, the alkylammonium cation is a quaternary alkylammonium ion.

The alkyl ammonium ion may be selected from the following: monomethylammonium, dimethylammoinium, trimethylammonium, tetramethylammonium, monoethylammonium, diethylammonium, triethylammonium, tetraethylammonium, monopropylammonium, dipropylammonium, tripropylammonium, tetrapropylammonium, monobutylammonium, dibutylammonium, tributylammonium and tetrabutylammonium.

Preferably, the alkylammonium cation is tetramethylammonium.

The alkyl ammonium cation may contain alkyl chains of varying lengths such as dimethyldiethylammonium.

Preferably, the substituted phosphonium cation is an alkylphosphonium cation. Preferably, the alkylphosphonium cation is a quaternary alkylphosphonium ion.

The alkyl phosphonium ion may be selected from the following: monomethylphosphonium, dimethylphosphonium, trimethylphosphonium, tetramethylphosphonium, monoethylphosphonium, diethylphosphonium, triethylphosphonium, tetraethylphosphonium, monopropylphosphonium, dipropylphosphonium, tripropylphosphonium, tetrapropylphosphonium, monobutylphosphonium, dibutylphosphonium, tributylphosphonium and tetrabutylphosphonium.

Preferably, the alkylphosphonium cation is tetramethylphosphonium.

The alkyl phosphonium cation may contain alkyl chains of varying lengths such as dimethyldiethylphosphonium.

In an alternate form of the present invention, the organic cation is an organic nitrogen-containing cation. More preferably, the organic nitrogen-containing cation is derived from ethylenediamine, pyrrole, imidazole, pyrazole, pyridine, pyrazine, pyrimidine or pyridazine. The organic nitrogen-containing cation may be selected from dimethylimidazolium or 2-(hydroxyalkyl)trialkylammonium compounds such as 2-(hydroxyethyl)trimethylammonium.

Advantageously, many quaternary alkylammonium ions and quaternary alkylphosphonium ions have a high degree of symmetry, leading to decreased polarity. Additionally, where provided, such alkyl moieties provide shielding to the charged nitrogen atom within the ion. As a result, the interactions between the electrical field and the quadrupole of $N_2$ will be suppressed considerably while the van der Waals interactions with $CH_4$ are less affected.

Preferably, the organic cation content of the porous support is at least 5% of the ion-exchangeable cations in the aluminosilicate. In one form of the invention, the organic cation content is at least 10% of the ion-exchangeable cations in the aluminosilicate. In an alternate form of the invention, the organic cation content is at least 20% of the ion-exchangeable cations in the aluminosilicate. In an alternate form of the invention, the organic cation content is at least 30% of the ion-exchangeable cations in the aluminosilicate. In an alternate form of the invention, the organic cation content is at least 40% of the ion-exchangeable cations in the aluminosilicate. In an alternate form of the invention, the organic cation content is at least 50% of the ion-exchangeable cations in the aluminosilicate. In an alternate form of the invention, the organic cation content is at least 60% of the ion-exchangeable cations in the aluminosilicate. In an alternate form of the invention, the organic cation content is at least 70% of the ion-exchangeable cations in the aluminosilicate. In an alternate form of the invention, the organic cation content is at least 80% of the ion-exchangeable cations in the aluminosilicate. In an alternate form of the invention, the organic cation content is at least 90% of the ion-exchangeable cations in the aluminosilicate. It will be appreciated that higher contents of organic cation provide increased selectivity of methane over nitrogen. It will be appreciated that due to steric hindrance and depending on the aluminosilicate and the organic cation, 100% conversion may not be possible.

Preferably, the selectivity for methane over nitrogen is at least 5.

The method of the present invention may be used with a wide range of gas sources, such as coal mining gas, biogas and LNG vent gas. 50% binary mixtures (e.g. coal mining gas, biogas) can be treated to increase the concentration of the methane component. Gas streams containing as little as 1% methane (e.g. LNG vent gas) may be purified by the method of the invention down to 100 ppm methane.

The present invention may be performed using any known adsorption technique such as pressure swing adsorption, vacuum swing adsorption, thermal swing adsorption, displacement purge or nonadsorbable purge (i.e. partial pressure reduction), dual reflux adsorption, or combination of the above.

It is desirable to utilize a pressure swing adsorption process at a temperature and pressure effective for adsorption and desorption of methane, with the temperature preferably maintained in the range −50° C. to 100° C., and more preferably from 0° C. to 70° C. The pressure during adsorption is preferably between about 10 psi to 2000 psi, preferably about 100 psi to 1500 psi, more preferably 500 psi to 1000 psi. The pressure during desorption is lower than during adsorption and is effective to cause the desorption of methane, preferably form about 0.1 torr to 150 psi, more preferably from about 0.1 torr to about 50 psi and most preferably from about 0.1 torr to about 25 psi.

In accordance with the present invention, there is provided an adsorbent comprising a porous support wherein the porous support comprises exchangeable cations and at least a portion of the exchangeable cations are organic cations.

The porous support may be selected from the group comprising silicates such as aluminosilicates, zeolites, zeolite-like metal-organic frameworks, molecular sieves, titanosilicates, layered hydroxides or hydrotalcites.

Alternatively, the porous support may be selected from the group comprising coordinated polymeric materials, including metal organic frameworks or carbonaceous materials.

Preferably, the porous support is a zeolite. Zeolites are crystalline aluminosilicates with open three dimensional framework structures built of, for example, $SiO_4$ and $AlO_4$ tetrahedra linked to each other by sharing all the oxygen atoms to form regular intra-crystalline cavities and channels of molecular dimensions. The electrovalence of the aluminium-containing tetrahedra is balanced by the inclusion of a cation, usually an alkaline metal or alkaline earth metal. It will be appreciated that zeolites may also comprise building blocks of $TiO_4$, $GaO_4$ and $FeO_4$.

The zeolite may be a natural zeolite or a synthetic zeolite. Zeolites that may be used in the present invention include ferrierite, brewsterite, stilbite, dachiardite, epistilbite, heulandite, chabazite and clinoptilolite.

In one form of the invention, the zeolite has faujasite topology. In an alternate form of the invention, the zeolite has Linde type A topology. In an alternate form of the invention, the zeolite has chabazite topology. Other suitable topologies include GME, LTL, MEI, MOZ and DFO as listed by the Structure Commission of the International Zeolite Association (http://izasc.ethz.ch/fmi/xsl/IZA-SC/ft.xsl).

Preferably, the zeolite is a Y zeolite. More preferably, the zeolite has a Si/Al ratio of 2-20. More preferably, the zeolite has a Si/Al ratio of 2.5-15. More preferably, the zeolite has a Si/Al ratio of 2.5-6.

The porous support preferably has pore diameters large enough to adsorb a hydrocarbon of interest.

Preferably, the hydrocarbon of interest is selected from C1-C4 saturated or unsaturated hydrocarbons. More preferably, the hydrocarbon is selected from a group containing methane, ethane, propane, butane, iso-butane, methylene, ethylene and propylene. Still preferably, the hydrocarbon is selected from methane and ethane. In a preferred form of the present invention, the hydrocarbon is methane.

It will be appreciated that the pore aperture size of the zeolite should be larger than the dimension of the organic cation to allow for the transfer of the organic cation into the cavity. As an example, tetramethylammonium (TMA) cations have a diameter of approximately 6 Å. Consequently, it is possible to exchange sodium ions with TMA ions in large pore zeolites for example, FAU types. It will be appreciated that if the dimensions of the organic cation and the pore aperture are close, such an ion exchange may not be experimentally viable due to limitation of mass transfer kinetics.

Preferably, the organic cation is an ionic liquid.

Preferably, the organic cation is selected from the following; substituted ammonium cations, substituted phosphonium cations and organic nitrogen-containing cations.

Preferably, the substituted ammonium cation is an alkylammonium cation.

Preferably, the alkylammonium cation is a quaternary alkylammonium ion.

The alkyl ammonium ion may be selected from the following: monomethylammonium, dimethylammoinium, trimethylammonium, tetramethylammonium, monoethylammonium, diethylammonium, triethylammonium, tetraethylammonium, monopropylammonium, dipropylammonium, tripropylammonium, tetrapropylammonium, monobutylammonium, dibutylammonium, tributylammonium and tetrabutylammonium.

Preferably, the alkylammonium cation is tetramethylammonium.

The alkyl ammonium cation may contain alkyl chains of varying lengths such as dimethyldiethylammonium.

Preferably, the substituted phosphonium cation is an alkylphosphonium cation. Preferably, the alkylphosphonium cation is a quaternary alkylphosphonium ion.

The alkyl phosphonium ion may be selected from the following: monomethylphosphonium, dimethylphosphonium, trimethylphosphonium, tetramethylphosphonium, monoethylphosphonium, diethylphosphonium, triethylphosphonium, tetraethylphosphonium, monopropylphosphonium, dipropylphosphonium, tripropylphosphonium, tetrapropylphosphonium, monobutylphosphonium, dibutylphosphonium, tributylphosphonium and tetrabutylphosphonium.

Preferably, the alkylphosphonium cation is tetramethylphosphonium.

The alkyl phosphonium cation may contain alkyl chains of varying lengths such as dimethyldiethylphosphonium.

In an alternate form of the present invention, the organic cation is an organic nitrogen-containing cation. More preferably, the organic nitrogen-containing cation is derived from ethylenediamine, pyrrole, imidazole, pyrazole, pyridine, pyrazine, pyrimidine or pyridazine. The organic nitrogen-containing cation may be selected from dimethylimidazolium or 2-(hydroxyalkyl)trialkylammonium compounds such as 2-(hydroxyethyl)trimethylammonium.

Preferably, the organic cation content of the porous support is at least 5% of the ion-exchangeable cations in the aluminosilicate. In one form of the invention, the organic cation content is at least 10% of the ion-exchangeable cations in the aluminosilicate. In an alternate form of the invention, the organic cation content is at least 20% of the ion-exchangeable cations in the aluminosilicate. In an alternate form of the invention, the organic cation content is at least 30% of the ion-exchangeable cations in the aluminosilicate. In an alternate form of the invention, the organic cation content is at least 40% of the ion-exchangeable cations in the aluminosilicate. In an alternate form of the invention, the organic cation content is at least 50% of the ion-exchangeable cations in the aluminosilicate. In an alternate form of the invention, the organic cation content is at least 60% of the ion-exchangeable cations in the aluminosilicate. In an alternate form of the invention, the organic cation content is at least 70% of the ion-exchangeable cations in the aluminosilicate. In an alternate form of the invention, the organic cation content is at least 80% of the ion-exchangeable cations in the aluminosilicate. In an alternate form of the invention, the organic cation content is at least 90% of the ion-exchangeable cations in the aluminosilicate. It will be appreciated that higher contents of organic cation provide increased selectivity of methane over nitrogen. It will be appreciated that due to steric hindrance and depending on the aluminosilicate and the organic cation, 100% conversion may not be possible.

BRIEF DESCRIPTION OF THE DRAWINGS

Further features of the present invention are more fully described in the following description of several non-limiting embodiments thereof. This description is included solely for the purposes of exemplifying the present invention. It should not be understood as a restriction on the broad summary, disclosure or description of the invention as set out above. The description will be made with reference to the accompanying drawings in which.

DESCRIPTION OF EMBODIMENTS

Figure 1:
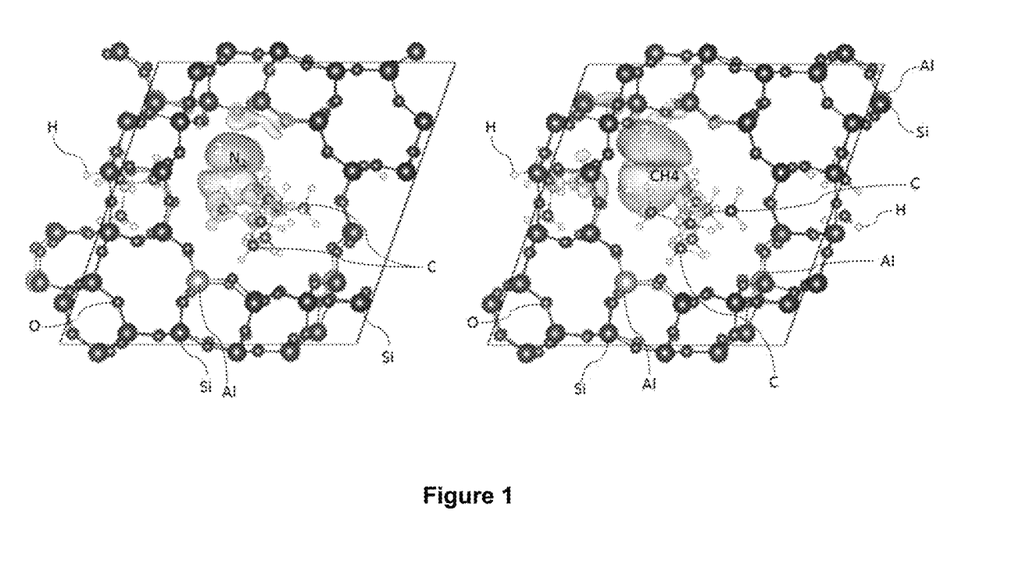
FIG. 1 shows a representation of ab initio DFT calculations used to estimate interaction energies.

Ab initio density functional theory (DFT) calculations show a $CH_4$ molecule (left panel of FIG. 1) binds much more strongly on TMAY (with 3 TMA+ per zeolite supercavity) than a $N_2$ molecule (right panel) does. Charge difference analysis of the DFT calculation shows much a greater charge redistribution for the adsorbed $CH_4$ molecule on TMAY than for $N_2$: charges accumulate (electron cloud 1) at the end of the gas molecules closest to the $TMA^+$ ion and deplete (electron could 2) from the gas molecule's other end.

It will be appreciated that higher degrees of $TMA^+$ saturation will substantially suppress the adsorption of $N_2$. Theoretical studies by DFT calculation show the energy of adsorption of $CH_4$ in a typical TMAY zeolite increased from 22.92 kJ/mol with one $TMA^+$ per supercavity, to 27.20 kJ/mol with two $TMA^+$, and eventually to 29.57 kJ with three $TMA^+$ per supercavity. By contrast, the energy of $N_2$ adsorption was not sensitive to the number of $TMA^+$ in the zeolite supercavity, with a change of less than 1.5 kJ/mol. Generally, the larger the difference in adsorption energy, the higher the adsorption selectivity in the low pressure region.

The pore volume of zeolites is normally between 9-30%, as shown in Table 1. A number of zeolite candidates (Table 2) were selected as potential parent frameworks for preparing adsorbents with organic cations, which may be referred to as Ionic Liquidic Zeolites (ILZ). However, this does not exclude the suitability of other medium/large pore zeolites.

TABLE 1

List of selected zeolites and their pore dimensions
(reference: http://izasc.ethz.ch/fmi/xsl/IZA-SC/ft.xsl).

| Zeolite type | Max radius (Å) | Max diffusible diameter (Å) | Accessible volume |
|---|---|---|---|
| FAU | 11.24 | 7.35 | 28% |
| LTA | 11.05 | 4.21 | 21% |
| AFR | 8.36 | 6.97 | 20% |
| AFS | 9.51 | 6.01 | 22% |
| AFY | 7.82 | 5.9 | 22% |
| ATS | 7.3 | 6.82 | 16% |
| BEA | 6.68 | 5.95 | 23% |
| BEC | 6.95 | 6.09 | 21% |
| BOF | 5.58 | 4.67 | 9% |
| BOG | 8.05 | 6.88 | 18% |
| BOZ | 8.71 | 4.92 | 23% |
| BHP | 9.51 | 6.01 | 22% |
| CGS | 5.86 | 4.01 | 11% |
| -CLO | 15.72 | 6.31 | 34% |
| CON | 7.45 | 5.6 | 19% |
| DFO | 11.29 | 7.19 | 22% |
| DON | 8.79 | 8.07 | 16% |
| EMT | 11.55 | 7.37 | 28% |
| EON | 7.83 | 6.79 | 13% |
| EZT | 6.57 | 6.13 | 13% |
| GME | 7.76 | 7.11 | 17.3% |
| IFR | 7.24 | 6.38 | 16% |
| IMF | 7.34 | 5.44 | 12% |
| IRR | 14.46 | 12.12 | 38% |
| ISV | 7.01 | 6.32 | 21% |
| ITR | 6.36 | 5.12 | 12% |
| -ITV | 9.32 | 6.98 | 38% |
| IWR | 7.48 | 5.91 | 19% |
| IWS | 8.25 | 6.66 | 23% |

TABLE 1-continued

List of selected zeolites and their pore dimensions
(reference: http://izasc.ethz.ch/fmi/xsl/IZA-SC/ft.xsl).

| Zeolite type | Max radius (Å) | Max diffusible diameter (Å) | Accessible volume |
|---|---|---|---|
| IWV | 8.54 | 7.03 | 22% |
| IWW | 7.07 | 6.25 | 15% |
| LTF | 8.16 | 7.5 | 11.6% |
| LTL | 10.01 | 7.5 | 15.4% |
| MAZ | 8.09 | 7.5 | 13.2% |
| MEI | 8.06 | 6.9 | 21.6% |
| MOZ | 10.03 | 7.54 | 13.1% |
| MOR | 6.7 | 6.45 | 12.6% |
| OFF | 7 | 6.61 | 15.1% |

TABLE 2

Examples of zeolites with large diffusible
diameter and accessible pore volumes.

| Zeolite name | Zeolite pore size (Å) | Max diffusible diameter (Å) | Accessible volume |
|---|---|---|---|
| FAU | 11.24 | 7.35 | 28% |
| -CLO | 15.72 | 6.31 | 34% |
| EMT | 11.55 | 7.37 | 28% |
| -ITV | 9.32 | 6.98 | 38% |
| MEI | 8.06 | 6.9 | 21.6% |
| DFO | 11.29 | 7.19 | 22% |
| LTL | 10.01 | 7.5 | 15.4% |
| MOZ | 10.03 | 7.54 | 13.1% |
| GME | 7.76 | 7.11 | 17.3% |

The zeolites of the present invention can be prepared by ion exchanging the existing cations in the aluminosilicate frameworks with organic cations or by synthesizing the aluminosilicate frameworks with organic cation templates.

Commercial NaY (CBV100 and CBV712) and NaX and laboratory made sodium chabazite (CHA) were tested for TMA exchange. Both the Y and X zeolites having the same crystal structure and topology, belong to the FAU family with a pore aperture diameter of 7.4 Å, whereas the chabazite zeolite belongs to the CHA family with a much smaller pore aperture, 3.8 Å in diameter.

Ion exchange of tetramethylammonium was conducted by shaking tetramethylammonium chloride and zeolite in a water bath at 40-70° C. for 0.5-15 hr. The mixture was centrifuged at 3000 rpm for 5 min and the solid component washed with deionized water. The centrifuge and washing steps were repeated. The solid component was shaken in a water bath with further tetramethylammonium chloride at 40-70° C. for at least 0.5-15 hr and centrifuged and washed as before two further times. The solid component was dried at no higher than 250° C.

The chemical compositions of the prepared TMAY and TMAX were confirmed by ICP-MS (inductively-coupled plasma mass spectrometry). The unit cell formula for TMAY and TMAX was $[C_4H_{12}N]_{8.1}Na_{18.9}Al_{27}SI_{69}O_{192}$ and $[C_4H_{12}N]_{3.7}Na_{38}Al_{41.7}Si_{54.3}O_{192}$, respectively, indicating that the corresponding degree of TMA saturation (i.e. ion exchange rate) was 31% and 9%, respectively. As discussed previously, lower TMA saturation in the X zeolite is believed to be a result of the cation density being too high to allow for higher degree of cation exchange due to space hindrance and diffusion limitation. This results in excessive metal cations sitting unexchanged in the cavity of the zeolites.

The crystal structure of the materials was verified by powder XRD. There was no change for the positions of the main peaks after ion exchange.

Figure 2:
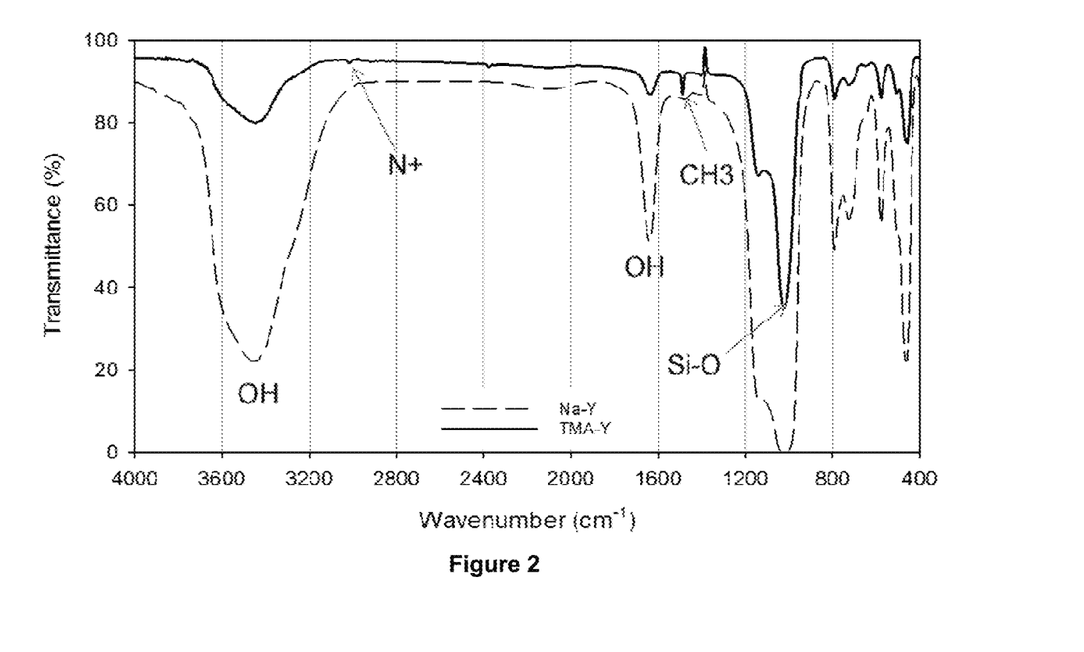
FIG. 2 is an FTIR plot demonstrating the existence of TMA+ in the zeolite.

The existence of TMA$^+$ in the zeolites was confirmed by FTIR as shown in FIG. 2 by the presence of the N$^+$ and CH$_3$ peaks.

Figure 3:
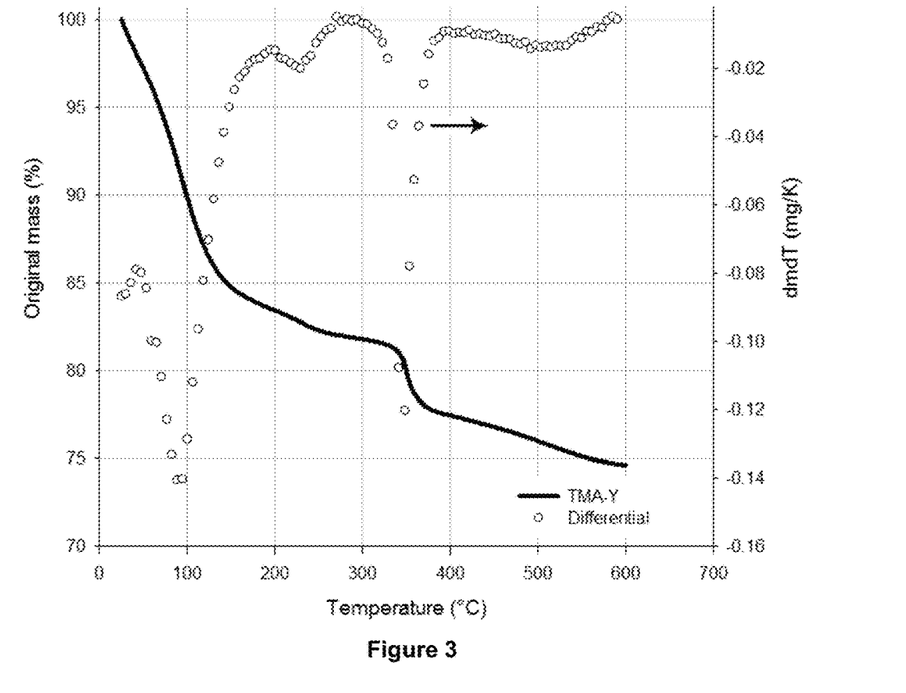
FIG. 3 is a TGA plot.

The thermal stability of the organic cation exchanged zeolites was verified by Thermal Gravimetric Analysis (TGA), which suggests the TMA-zeolites are stable up to 573 K as shown in FIG. 3.

The synthesized TMAY (Si/Al=2.55) with 31% TMA$^+$ exchange contained 8 TMA$^+$ per unit cell, which is equivalent to no more than 4 TMA$^+$ per supercavity. This admits the possibility of having TMA$^+$ sitting in the passage connecting two supercavities. Though full saturation of TMA$^+$ in FAU is desired, it is unlikely achievable in practice because of (1) the lack of space for diffusion of the large organic cations inside some cavities and (2) the maximum exchange rate diminishes with a decrease in the Si/Al ratio, i.e. increase of cation density. The adsorption equilibrium experiments of TMAX and TMAY suggest FAU zeolites with a higher degree of TMA saturation have a higher CH$_4$-to-N$_2$ selectivity.

TMAY powder was pressurized into 1-2 mm pellets with a 50 ton high pressure pelletizer (XRF Scientific Instruments). The TMAY pellets (5.36 g dry base) were preactivated at 593 K under vacuum on a Micromeritics ASAP2020 for 24 hr.

Single-component isotherms of N$_2$ and CH$_4$ adsorption on TMAY were collected at temperatures ranging from 243 K to 323 K and pressures up to 120 kPa using a standard volumetric method on a Micromeritics ASAP2020 accelerated surface area and porosity analyzer. The surface area and DFT pore size distribution of the prepared samples were measured by N$_2$ adsorption at 77 K. Prior to each measurement, the samples were thoroughly dehydrated and degassed on a Micromeritics ASAP2020 analyzer by stepwise heating (1 K/min) up to 593 K and held at 593 K under high vacuum for 300 min and then cooled to 295 K followed by backfill with helium.

Figure 4:
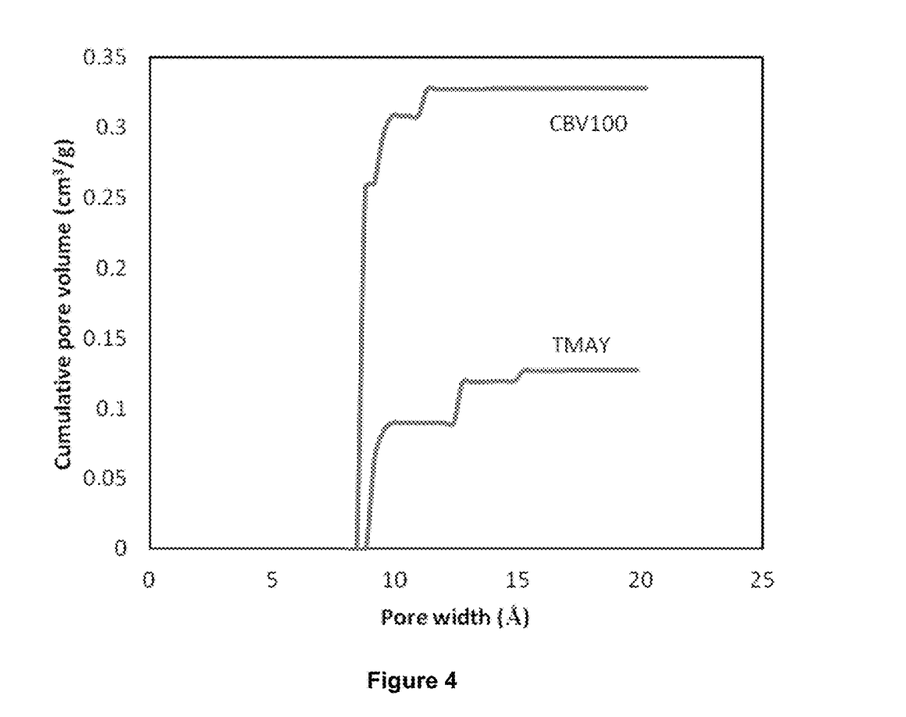
FIG. 4 is a plot of the change in parent NaY zeolite (CBV100) upon 31% exchange of its $Na^+$ ions with $TMA^+$ ions, showing the zeolite's cumulative pore volume as a function of pore size before and after ion exchange.

Larger accessible pore volumes also allow for higher adsorption capacity at very high pressures. As shown in FIG. 4, the pore volume of FAU zeolite is reduced by 60% after exchanging 30% of the original Na$^+$ by TMA$^+$. However, this should not affect the loading of CH$_4$ at low and medium pressures. For example, experimental data in FIG. 5 suggests CH$_4$ capacity was even improved by 15% at 1 bar pressure after TMA$^+$ exchange.

Figure 5:
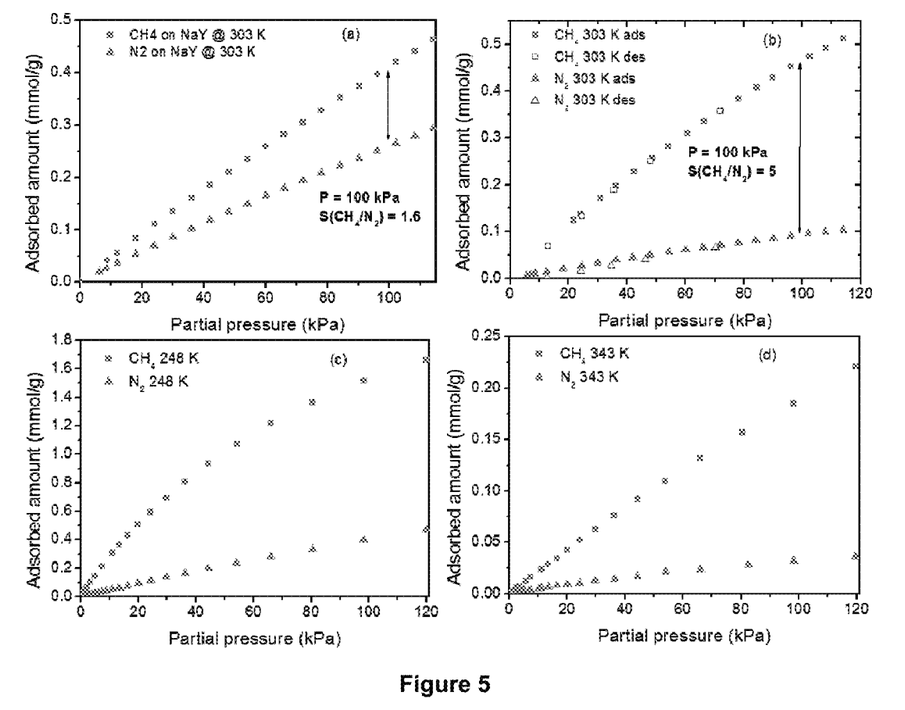
FIG. 5 is a plot of single component ($CH_4$ or $N_2$) adsorption isotherms on parent zeolite NaY (a) and ion exchanged TMAY (b, c, d)

FIG. 5 shows a plot of single component (CH4 or N2) adsorption isotherms on parent zeolite NaY (a) and ion exchanged TMAY (b, c, d). The calculated CH$_4$/N$_2$ selectivity is improved by 300% in TMAY compared with parent NaY; CH$_4$ capacity is improved by 15.

Figure 6:
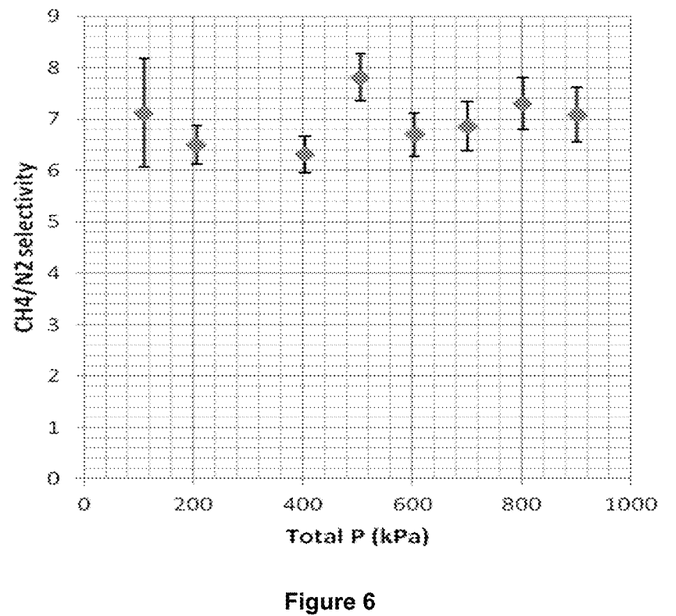
FIG. 6 is a plot of $CH_4/N_2$ selectivity for their equimolar binary mixture on ionic liquidic zeolite TMA-Y at 248 K.

Following preactivation, TMAY pellets were transferred into a stainless-steel adsorption column (⅜ in. diameter, 16 cm long) and flushed with helium for 1 hr. Binary CH$_4$/N$_2$ adsorption isotherms on TMAY were measured with a dynamic column breakthrough (DCB) apparatus as known in the art. Binary breakthrough experiments were carried out at 248 K, 273 K and 303 K respectively in the pressure range of 103.8-902.8 kPa by feeding CH$_4$/N$_2$ gas mixtures (with CH$_4$ mole fraction of 0.064-0.914) at a flow rate of 50 mL/min at STP set by mass flow controllers. All component gases used were supplied by BOC with the flowing fractional purities: He 99.999%, CH$_4$ 99.995%, and N$_2$ 99.999%. FIG. 6 shows that tetramethylammonium-Y zeolite, has a CH$_4$/N$_2$ selectivity constantly between 6 and 8 for binary equimolar mixtures of $CH_4+N_2$ at 248 K up to the maximum tested pressure of 9 bar. Importantly this selectivity was achieved without loss of $CH_4$ capacity. That the TMAY maintained high $CH_4/N_2$ selectivity even at high pressures is particularly advantageous for the gas industry for two reasons: (1) most of the upstream and downstream gas processes are operated at elevated pressures and thus a high pressure $CH_4/N_2$ separation will help to retain the energy; (2) high pressure $CH_4/N_2$ separation process will also reduce the column size and the cost.

Figure 7:
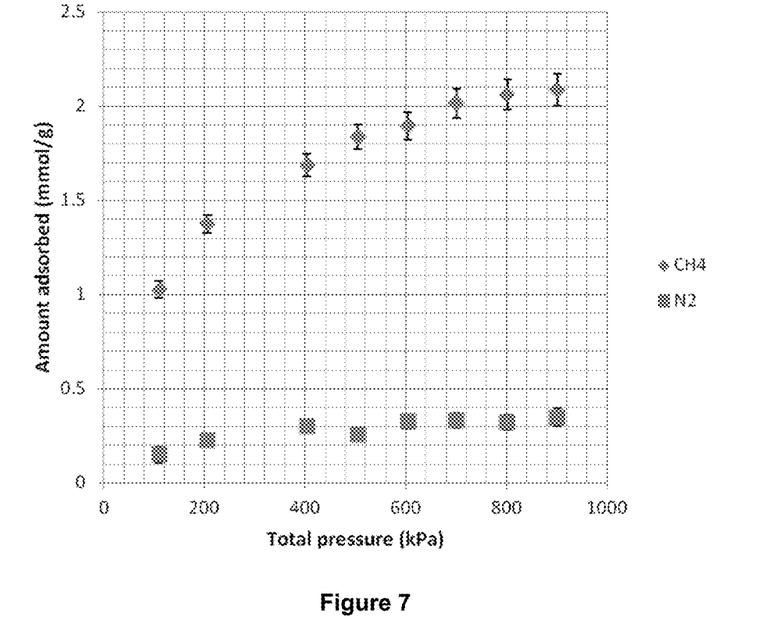
FIG. 7 shows a binary isotherm of equimolar $CH_4+N_2$ on TMA-Y at 248 K.

FIG. 7 shows the $CH_4$ capacity at 248 K reaches as high as 2.1 mmol/g in the binary equimolar mixture of $CH_4$ and $N_2$.

Figure 8:
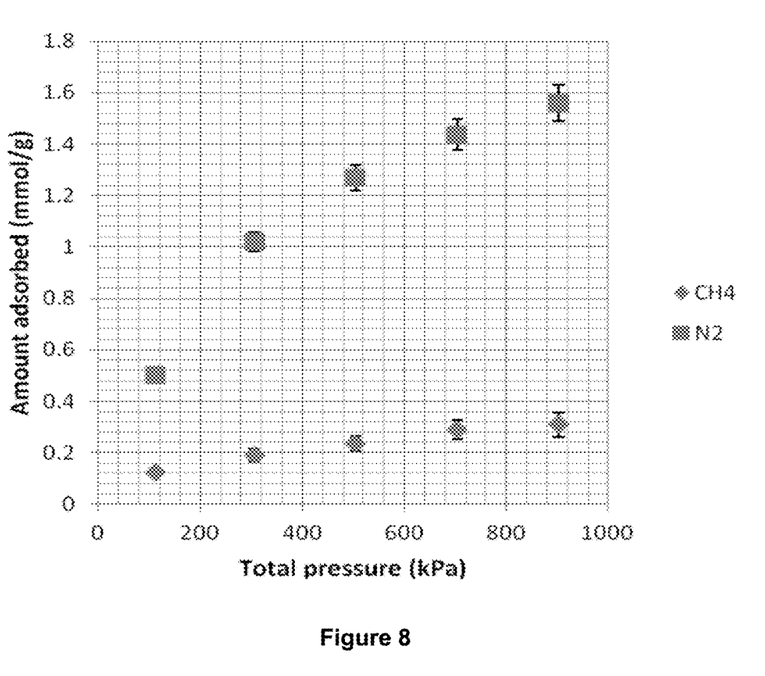
FIG. 8 shows binary isotherms of equimolar $CH_4+N_2$ on TMA-Y at 273 K.
Figure 9:
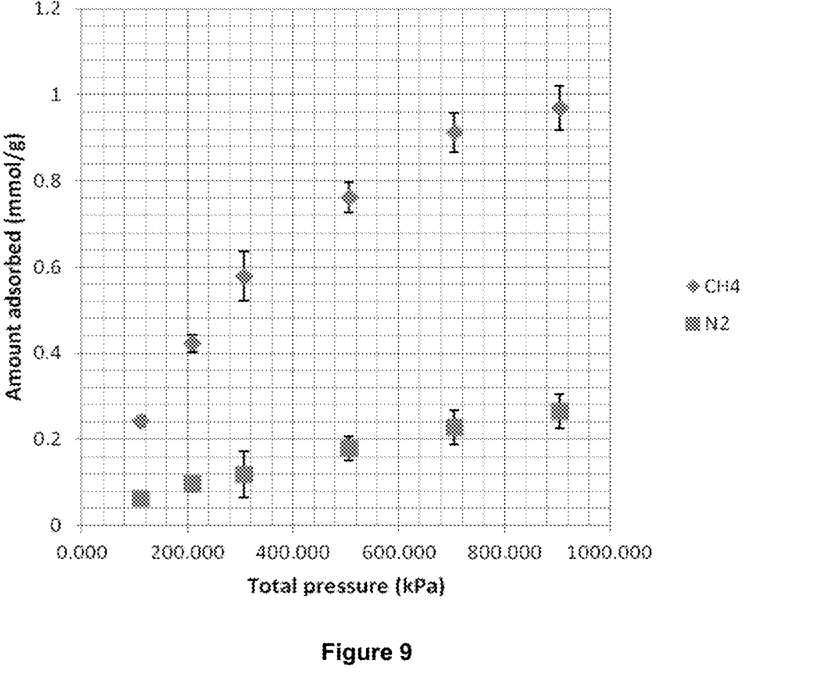
FIG. 9 shows binary isotherms of equimolar $CH_4+N_2$ on TMA-Y at 303 K.

FIGS. 8 and 9 present the results of binary adsorption isotherms at 273 K and 303 K respectively.

Figure 10:
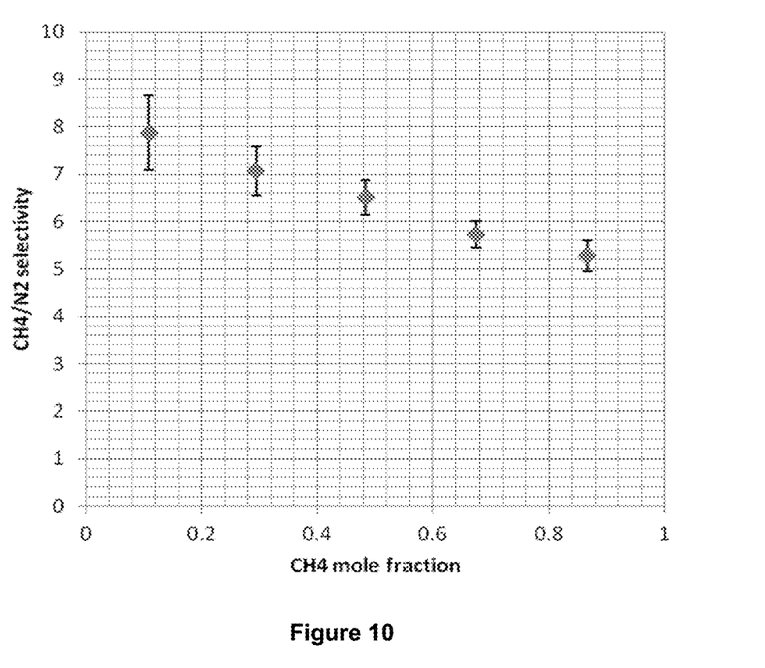
FIG. 10 is a plot of $CH_4/N_2$ selectivity as a function of composition at a fixed total pressure of 2 bar and 248 K.
Figure 11:
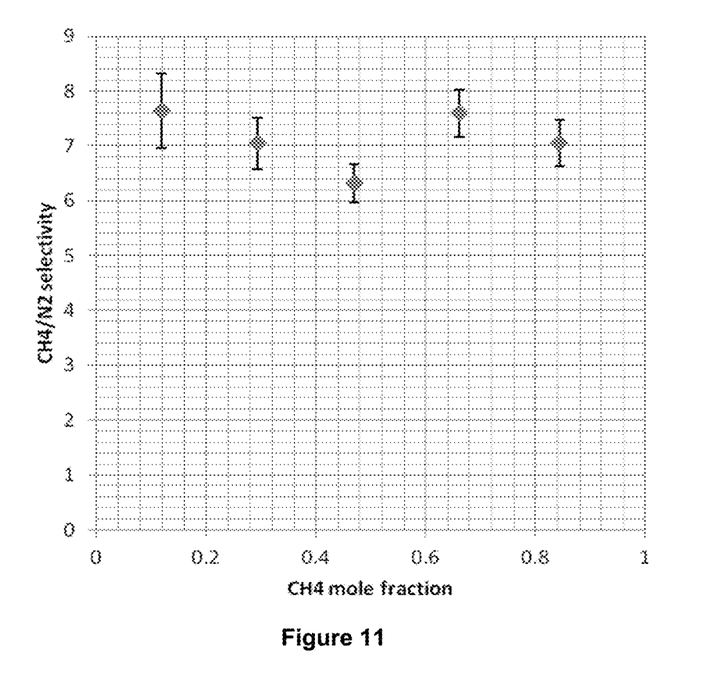
FIG. 11 is a plot of $CH_4/N_2$ selectivity as a function of composition at a fixed total pressure of 4 bar and 248 K.

FIG. 10 presents the results of $CH_4/N_2$ selectivity at 2 bar and 248 K as a function of $CH_4$ mole fraction. FIG. 11 presents the results of $CH_4/N_2$ selectivity at 4 bar and 248 K as a function of $CH_4$ mole fraction.

Figure 12:
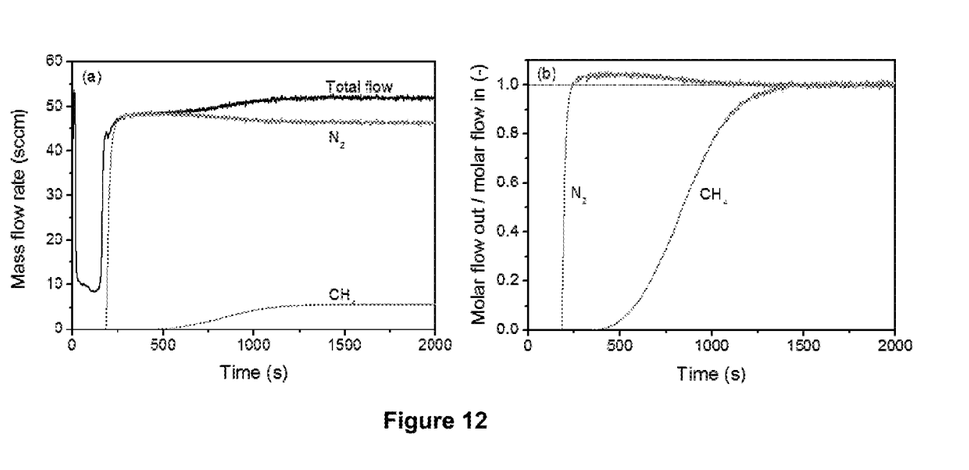
FIG. 12 is a plot of the binary breakthrough of 10% $CH_4$+90% $N_2$ at 2 bar pressure and 248 K temperature from a bed of TMA-Y: (a) outlet mass flows, and (b) normalized molar flows.

FIG. 12 is a plot of the binary breakthrough of 10% $CH_4$+90% $N_2$ at 2 bar pressure and 248 K temperature from a bed of TMA-Y: (a) outlet mass flows, and (b) normalized molar flows. The data in FIG. 12 can be used to show that the rate of adsorption by either $N_2$ or $CH_4$ is fast (similar to the parent zeolite), which means that the selectivities being observed here are equilibrium properties of the material.

Figure 13:
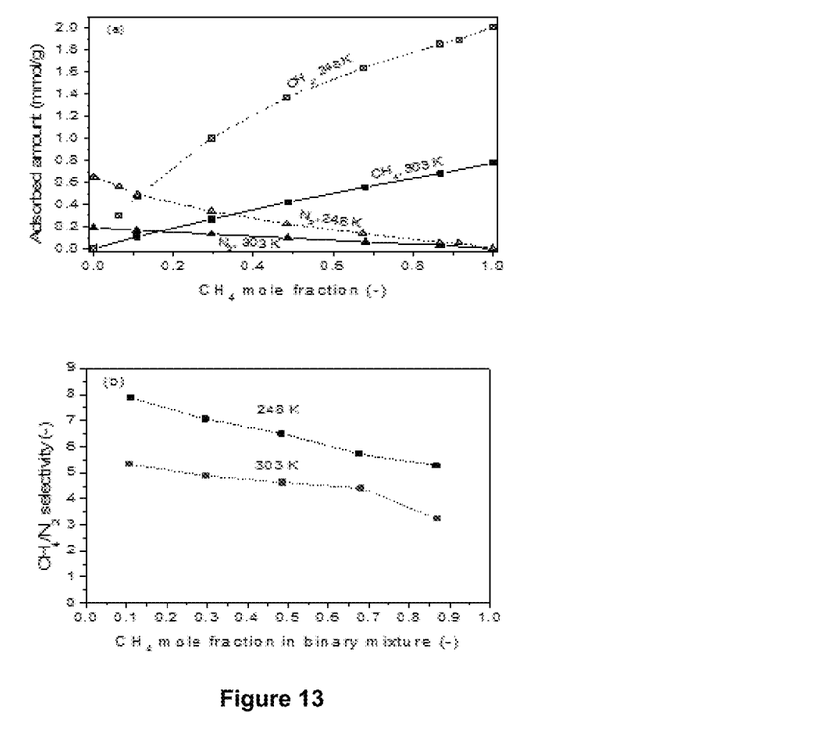
FIG. 13 is a binary isotherm (a) and selectivity (b) with varying composition and fixed total pressure of 2 bar.

FIG. 13 shows the $CH_4$ capacity at 248 K reaches 2.0 mmol/g at 2 bar.

A simulation of a 10-step two column PSA process using TMAY to treat an equimolar binary mixture of $CH_4+N_2$ using TMAY achieved 94.1% $CH_4$ product purity and 94.4% recovery with the following conditions Column physical size: ID=100 mm L=1.8 m
Adsorbent: TMAY, 2 mm pellet
Feed flow rate: 130.5 liter per minute (standard)
Pressure: 3.0 bar
Temperature: 30° C.

Figure 14:
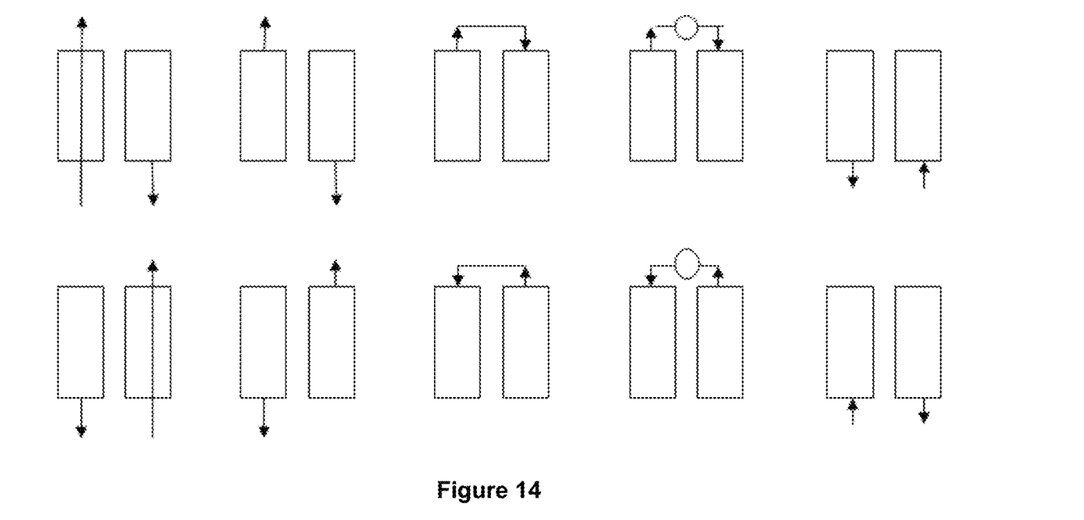
FIG. 14 is a schematic representation of a PSA process.
Figure 15:
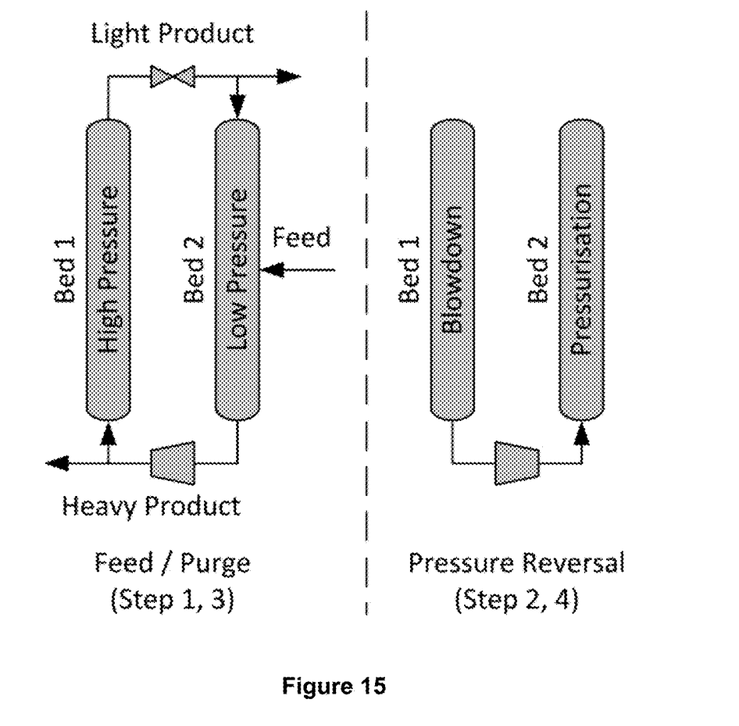
FIG. 15 is a schematic of the dual-reflux PL-A cycle. The second half of the cycle is the same but with the adsorption bed numbering reversed. The combined pressurization and blowdown step is called the pressure reversal step.

The ten step process is represented schematically at FIG. 14 wherein the steps are as follows:
Step 1: adsorption
Step 2: blow down to 1 bar
Step 3: pressure equalization
Step 4: depressurization/purge to the other column
Step 5, 6 and 7: desorption/evacuation
Step 8 and 9: pressurization/equalization from the other column
Step 10: re-pressurization Experiments using a four-step dual-reflux pressure swing adsorption process schematically represented in FIG. 15 to treat a 2.6% dilute $CH_4$ achieved 22 times enrichment of methane with 99.9% recovery, with the following conditions:

TABLE 3

The operating parameters that were held constant across all experiments. The valve positions in FIG. 15 correspond to Step 1 (left) and Step 2 (right).

| Cycle Parameters | |
| --- | --- |
| Feed/Purge Time | 120 s |
| Pressurisation/Blowdown Time | 90 s |
| High Pressure | 5.0 bar |
| Low Pressure | 1.4 bar |
| Pressure Ratio | 3.6 |

TABLE 3-continued

The operating parameters that were held constant across all experiments. The valve positions in FIG. 15 correspond to Step 1 (left) and Step 2 (right).

| | Column 1 | Column 2 |
| --- | --- | --- |
| Step 1 | HP Heavy Purge | LP Feed/Light Purge |
| Step 2 | Blowdown | Pressurisation |
| Step 3 | LP Feed/Light Purge | HP Heavy Purge |
| Step 4 | Pressurisation | Blowdown |

| Feed Parameters | |
| --- | --- |
| Flowrate | 1.25 SLPM |
| Pressure | 1.4 bar |
| Temperature (atmospheric) | 20-25° C. |
| Fractional Axial Feed Position | 0.5 |

Isothermal equilibrium adsorption for single component gas of $O_2$, CO, $C_2H_6$ and $C_3H_8$ was tested on TMAY, respectively. At 298 K and 100 kPa total pressure, the determined selectivity (based on direct comparison between the uptakes of two gases at same partial pressure) for the above gases are $CH_4/O_2$=5.28, $CH_4/CO$=2.97, $C_2H_6/CH_4$=4.66, $C_3H_8/CH_4$=2.71.

Other ionic liquidic zeolites (FAU framework) containing organic cations of dimethylamine and trimethylamine have been prepared as described above. Elemental analysis of the resultant products shows the DMA-Y has a cation exchange rate of 60% and the TriMA-Y has 42%, in comparison with 30% for TMA-Y, which is consistent with the size of the organic cations, i.e. smaller organic cations allows for higher exchange rate.

Figure 16:
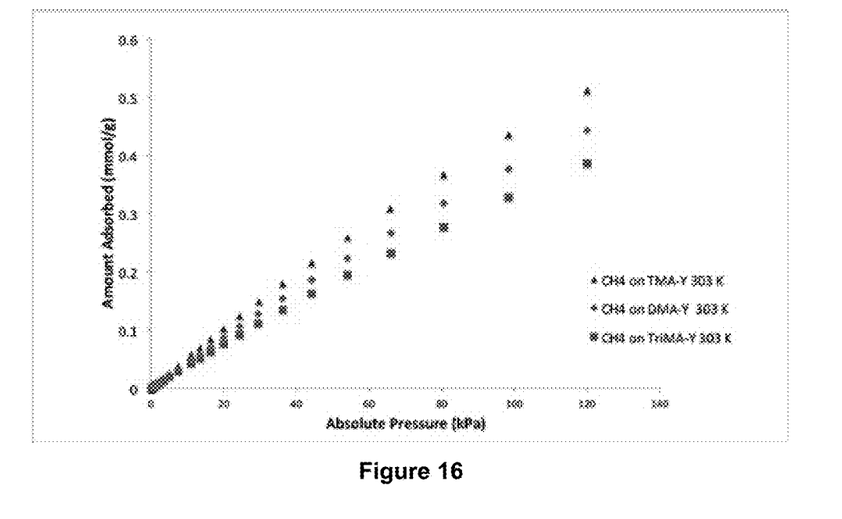
FIG. 16 shows the capacity of three FAU type ILZ materials to adsorb $CH_4$ (support at paragraph 0127).

FIG. 16 shows the $CH_4$ capacity on three of the FAU type ILZ materials, namely DMA-Y, TriMA-Y, and TMA-Y. It is noticeable that TMA-Y has the highest capacity for $CH_4$ adsorption. Further study suggests the $CH_4/N_2$ selectivity on TMA-Y remains the highest among the three samples.

Throughout this specification, unless the context requires otherwise, the word "comprise" or variations such as "comprises" or "comprising", will be understood to imply the inclusion of a stated integer or group of integers but not the exclusion of any other integer or group of integers.

What is claimed is:

1. A method for separating methane from a feed containing a mixture of at least methane and nitrogen, comprising contacting the feed with an adsorbent comprising a porous support, where upon contacting the adsorbent methane is adsorbed selectively over nitrogen, wherein the porous support comprises exchangeable cations and at least a portion of the exchangeable cations are organic cations, wherein the porous support has pore diameters large enough to adsorb methane.

2. A method for separating methane from a feed containing a mixture of at least methane and nitrogen according to claim 1, wherein the porous support is selected from coordinated polymeric materials, including metal organic frameworks, aluminosilicates, zeolites, zeolite-like metal-organic frameworks, molecular sieves, titanosilicates, layered hydroxides or hydrotalcites.

3. A method for separating methane from a feed containing a mixture of at least methane and nitrogen according to claim 1, wherein the porous support is a zeolite, where the zeolite is selected from the group consisting of ferrierite, brewsterite, stilbite, dachiardite, epistilbite, heulandite and clinoptilolite, and where the zeolite has faujasite, Linde type A or chabazite topology.

4. A method for separating methane from a feed containing a mixture of at least methane and nitrogen according to claim 3, wherein the zeolite has a Si/Al ratio of 2-20.

5. A method for separating methane from a feed containing a mixture of at least methane and nitrogen according to claim 1, wherein the organic cation is from an ionic liquid, including organic cations such as a substituted ammonium cation, a substituted phosphonium cation or an organic nitrogen-containing cation, or where the organic cation is selected from the group consisting of monomethylammonium, dimethylammoinium, trimethylammonium, tetramethylammonium, monoethylammonium, diethylammonium, triethylammonium, tetraethyl ammonium, monopropyl ammonium, dipropylammonium, tripropylammonium, tetrapropylammonium, monobutylammonium, dibutyl ammonium, tributyl ammonium and tetrabutyl ammonium.

6. A method for separating methane from a feed containing a mixture of at least methane and nitrogen according to claim 1, wherein the organic cation content of the porous support is at least 5% of the ion-exchangeable cations in the aluminosilicate; at least 10% of the ion-exchangeable cations in the aluminosilicate; at least 20% of the ion-exchangeable cations in the aluminosilicate; at least 30% of the ion-exchangeable cations in the aluminosilicate; at least 40% of the ion-exchangeable cations in the aluminosilicate; at least 50% of the ion-exchangeable cations in the aluminosilicate; at least 60% of the ion-exchangeable cations in the aluminosilicate; at least 70% of the ion-exchangeable cations in the aluminosilicate; at least 80% of the ion-exchangeable cations in the aluminosilicate at least 90% of the ion-exchangeable cations in the aluminosilicate.

7. A method for separating methane from a feed containing a mixture of at least methane and nitrogen according to claim 1, wherein, the selectivity for methane over nitrogen is at least 5.

8. A method for separating methane from a feed containing a mixture of at least methane and nitrogen according to claim 1, wherein the feed includes coal mining gas, biogas and LNG vent gas.

* * * * *